United States Patent [19]
Jackson

[11] Patent Number: 5,980,523
[45] Date of Patent: Nov. 9, 1999

[54] TRANSVERSE CONNECTORS FOR SPINAL RODS

[76] Inventor: Roger Jackson, 4706 W. 86th St., Prairie Village, Kans. 66207

[21] Appl. No.: 09/004,416

[22] Filed: Jan. 8, 1998

[51] Int. Cl.$^6$ .................................................. A61B 17/56
[52] U.S. Cl. ............................................................ 606/61
[58] Field of Search ...................................... 606/60, 61

[56] References Cited

U.S. PATENT DOCUMENTS

| | | | |
|---|---|---|---|
| 5,005,562 | 4/1991 | Cotrel | 606/61 |
| 5,047,029 | 9/1991 | Aebi et al. | 606/61 |
| 5,261,907 | 11/1993 | Vignaud et al. | 606/60 |
| 5,261,909 | 11/1993 | Sutterlin et al. | 606/61 |
| 5,397,363 | 3/1995 | Gelbard | 623/17 |
| 5,403,316 | 4/1995 | Ashman | 606/61 |
| 5,624,442 | 4/1997 | Mellinger et al. | 606/61 |
| 5,716,355 | 2/1998 | Jackson | 606/61 |

*Primary Examiner*—Michael Buiz
*Assistant Examiner*—David O. Reip
*Attorney, Agent, or Firm*—Litman, Kraai, & Brown, L.L.C.; John C. McMahon

[57] ABSTRACT

An improved system of transverse connectors for fixing the relative alignment of spinal rods in an osteosynthesis apparatus which can accommodate variations in the divergence and skew of the spinal rods and arch along a connector. In one embodiment of the invention a rotating hooked connector includes a shaft which is rotatably and slidably securable within a shaft receiving bore in a base hooked connector. Hooked ends of the connectors are secured to the spinal rods. Once a desired alignment of the rotating hooked connector is established relative to the base hooked connector to accommodate the orientation of the spinal rods, the alignment of the two connectors is fixed utilizing a set screw threadingly advanced into engagement with the shaft through a threaded bore in the base hooked connector. In an alternative embodiment the hooked end of the rotating hooked connector is connected to shaft thereof by a flanged screw such that the pivotal relationship of the shaft and hooked end is adjustable until the flanged screw is tightened to fix the pivotal relationship. In another embodiment, the shaft receiving bore of the base connector extends through a pivot mount which is pivotally mounted to a support arm of the base connector.

16 Claims, 5 Drawing Sheets

TRANSVERSE CONNECTORS FOR SPINAL RODS

BACKGROUND OF THE INVENTION

The present invention relates to improvements in transverse connectors for use in making connections between two spinal rods that are placed along a patient's spine during spinal osteosynthesis procedures.

Surgically implanted spinal osteosynthesis apparatus often includes a pair of rods which are secured along at least a portion of the spine on opposite sides thereof by a system of hooks, bone screws including sacral screws and pedicle screws and transverse connectors for the purpose of stabilizing and adjusting spinal alignment.

Although in a preferred system the spinal rods would be in parallel alignment, the rods are seldom parallel in practice. Placement of the rods in a skewed alignment is often necessary to produce the desired corrective or supporting forces on the spine. In practice the rods may be co-planar but not parallel or may be non co-planar. In some instances the rods are non co-planar and transversely divergent. Each of these non parallel configurations produces difficulty with respect to the joining of connectors to the rods, since rod receiving heads of the connectors are most stable when they join perpendicular with respect to the rods. If the rods themselves are not parallel, the connectors cannot form the most stable juncture with the rod, if the connectors are straight and cannot be bent to the most suitable configuration for joining. In addition the location of spinal processes sometimes requires that a connector have an arch that is adjustable to just clear the spinal process such that the connector does not protrude further rearward of the spine than is necessary. Preferred transverse connection systems will readily permit variations in the alignment of the rods while providing fast securement resistant to slipping or dislocation.

SUMMARY OF THE INVENTION

A set of rod connectors is provided that provide for twisting or rotation of the connector about the longitudinal axis thereof, provide for bending from side to side relative to the connector, provide for arching of the connector to avoid bone and to provide for any configuration thereof. The set of connectors also allows variable adjustment of the various connectors to adjust for an infinite selection of possible configurations to adjust for any skewed or twisted combination of rods.

In the present invention comprises an improved system of transverse connectors for fixing the relative alignment of spinal rods in an osteosynthesis apparatus which can accommodate variations in the divergence and skew of the spinal rods (that is, the non parallel configurations of the rods) and can adjust for arc of the connector where necessary.

In one embodiment of the invention a rotating hooked connector includes a shaft which is rotatably and slidably securable within a cylindrical bore in a base hooked connector. Hooked ends of the connectors are secured to skewed spinal rods. Once a desired alignment of the first hooked connector is established relative to the second hooked connector by rotation of the shaft in the bore to accommodate the orientation of the spinal rods such that the hooked ends are perpendicular to the rods, the alignment of the two connectors is fixed utilizing a set screw threadingly advanced into engagement with the shaft through a threaded bore in the base hooked connector.

In an alternative embodiment the rotating hooked connector is formed from a rotating link which includes the shaft and a hooked pivot connector which includes the hooked end. The rotating link and hooked pivot connector each include an eyelet which are adapted to be positioned in overlapping alignment such that the two components may be secured together by a flanged screw extending through the eyelet. Until the screw is fully tightened, the pivotal orientation of the rotating link and hooked pivot connector is adjustable to accommodate variances in the degree of divergence of spinal rods to which the connection system is to be attached. Once the rotating link and the hooked pivot connector are positioned in the desired alignment, the relative orientation thereof is fixed by tightening of the flanged screw.

In another embodiment of the present invention two hooked pivot connectors are secured to the aligned spinal rods and a cross link having eyelets on each end thereof is used to secure the hooked pivot connectors together utilizing flanged screws. The orientation of each of the hooked pivot connectors is pivotally adjustable relative to the cross link prior to tightening of the flanged screws to allow for divergence of the rods (that is, where the rods are co-planar but not parallel).

Another embodiment of the present invention, utilizes a rotating link secured to a hooked pivot connector generally as noted above wherein the pivotal relationship between the rotating link and the hooked pivot connector is adjustable. A hooked base connector incorporates a pivot mount pivotally or swivelly connected to a support arm of the base connector and having a bore extending therethrough for receiving the shaft of the rotating link. The pivot mount is rotatably mounted in a recess in the support arm such that a leading edge of the shaft receiving bore extends into the recess. A set screw receiving bore extends through the pivot mount and into the shaft receiving bore from an opposite side of the recess, such that advancement of the set screw into the bore and against the shaft drives the shaft against the face of the support arm, fixing the orientation of the shaft relative to the support arm. This embodiment is particularly well adapted for forming a connection between spinal rods wherein the connector must arch and otherwise adjust because a portion of the spine forms an obstruction to a direct connection.

The transverse connection sets of the present invention are particularly well adapted to utilize a style of set screw or flanged screws having break off heads which facilitate installation.

OBJECTS AND ADVANTAGES OF THE INVENTION

The objects and advantages of the invention include: providing a transverse connection system for spinal rods which readily accommodates variations in the degree of divergence of the spinal rods such that the ends of each associated connector mates correctly with an associated rod; providing a transverse connection system for spinal rods which readily accommodates variations in the degree of skew of the spinal rods again such that ends of connectors mates correctly with the rods; providing a transverse connection system for spinal rods which readily accommodates variations in the degree of divergence and skew of the spinal rods; providing a transverse connection system for spinal rods to form a connection between spinal rods at a position where a straight connection between the rods is obstructed by bone or the like; providing such a system in which the configuration or orientation of the connection system is initially infinitely moveable parts variable in many aspects by adjustment and movement of without requiring actual physical bending of the rods to make adjustments to accommodate variations in divergence or skew and subsequent to adjustment the orientation may be securely fixed by the installing surgeon; providing such a system which is relatively easy to install; providing such a system which has a relatively low profile and occupies a relatively small space when implanted; and providing such a system which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
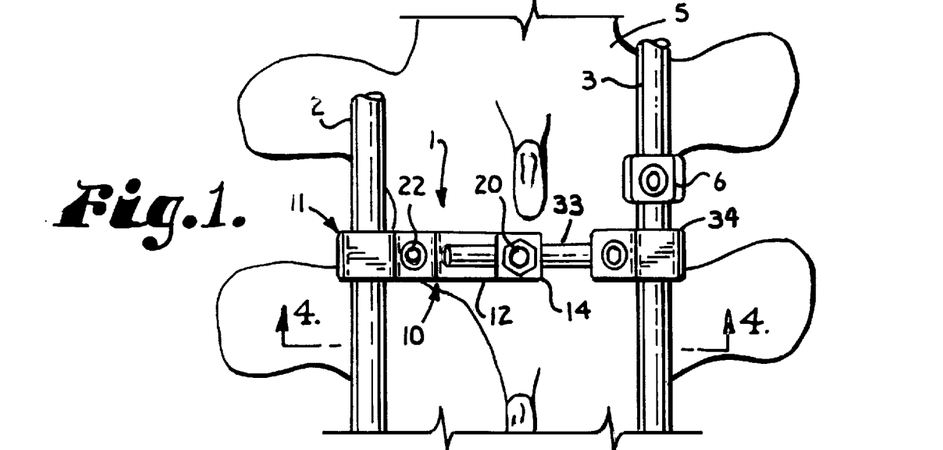
FIG. 1 is a fragmentary posterior view of a spinal column with a corrective implant system incorporating a pair of rods and a first transverse connection system of the present invention.
Figure 2:
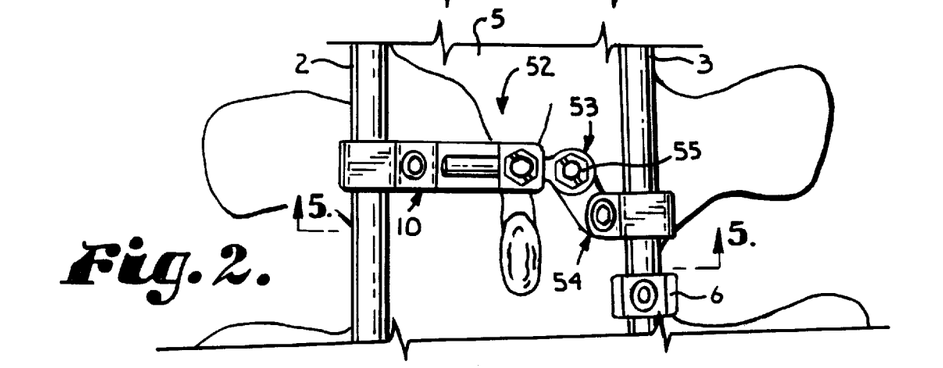
FIG. 2 is a fragmentary posterior view of a spinal column with a corrective implant system incorporating a second transverse connection system of the present invention.
Figure 3:
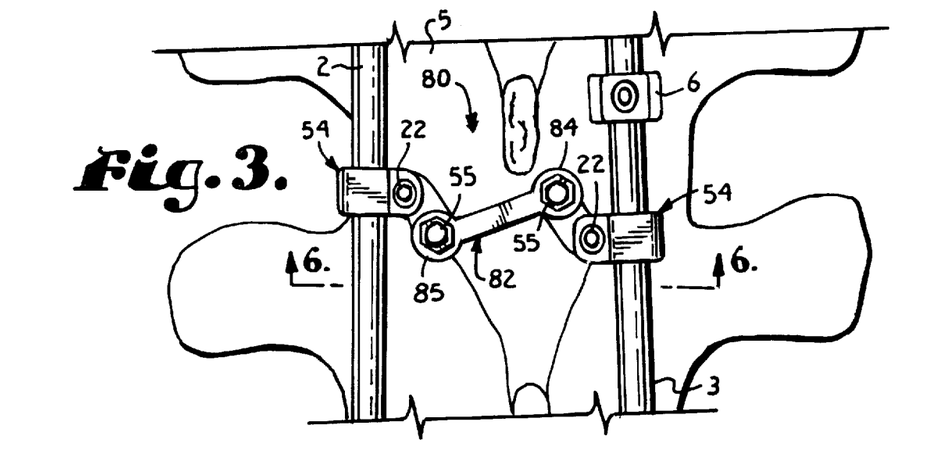
FIG. 3 is a fragmentary posterior view of a spinal column with a corrective implant system incorporating a third transverse connection system of the present invention.

Referring to the drawings in more detail, the reference numeral 1 generally refers to a first transverse connection system, connecting spinal rods 2 and 3. The spinal rods 2 and 3 are secured along opposite sides of the spine or spinal column 5 by bone screws 6, a few of which are shown in FIGS. 1 through 3.

Figure 4:
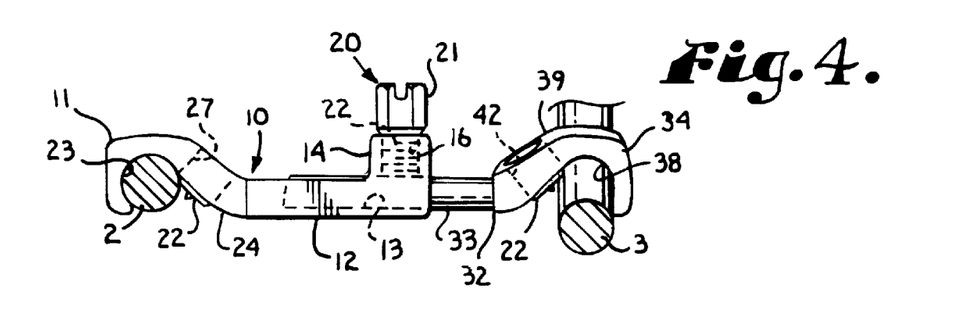
FIG. 4 is an enlarged and fragmentary cross-sectional view, taken along line 4—4 of FIG. 1.

The first transverse connection system 1 comprises a base connector 10 having a first hooked end 11 and an elongated bearing arm 12. A cylindrical bore 13, see FIG. 4, is formed in the bearing arm 12 and a boss 14 is formed on a distal end of the bearing arm 12. A threaded bore 16 is formed in the boss 14 in communication with and perpendicular to the cylindrical bore 13. The threaded bore 16 is adapted to receive a set screw 20 having a break-off head 21 and a lower threaded portion 22, as described in more detail below.

A rod receiving groove 23, sized to receive a spinal rod 2 or 3, extends into the hooked end 11. The connection system is adjusted, as described below, such that the rod 2 or 3 fits snugly and correctly into the associated groove 23 such that the radius of the groove 23 is perpendicular to the axis of the rod 2 or 3 where the two are connected. The hooked end 11 also includes a neck or stem portion 24 which forms a transition with the bearing arm 12. A threaded bore 27, sized to receive a set screw 20 (only the lower portion 22 of which is shown in FIGS. 1 and 4), extends through the neck portion 24 and into the rod receiving groove 23. Once a spinal rod 2 or 3 has been positioned within the rod receiving groove 23, the associated set screw 20 may be threadedly advanced through the threaded bore 27, such that the lower threaded portion 22 engages a respective spinal rod 2 or 3 generally tangentially thereto and biases the rod 2 or 3 to the opposite side of the groove 23 and into engagement with an inner surface of the hooked end 11 to secure the spinal rod 2 or 3 within the groove 23 and prevent rotation or sliding of the base connector 10 relative thereto. The head 21 of the set screw 20 is intentionally sheared off during installation at a preselected torque, as discussed in more detail below.

The first transverse connection system 1 also includes a hooked rotating connector 32 having a cylindrical shaft 33 and a second hooked end 34. The cylindrical bore 13 in the bearing arm 12 is sized to receive the cylindrical shaft 33 of the hooked rotating connector 32 to permit rotation of the rotating connector 32 relative to the base connector 10 and to permit the hooked end 34 of the rotating connector 32 to be slidingly advanced toward and away from the hooked end 11 of the base connector 10.

The second hooked end 34 is of similar construction as the first hooked 11 end and includes a rod receiving groove 38 formed therein which is sized to receive an opposite spinal rod 2 or 3 of a pair. The second hooked end 34 also includes a neck or stem portion 39. The neck portion 39 forms a transition with the cylindrical shaft 33. A threaded bore 42, sized to receive a set screw 20 (only the lower threaded portion 22 of which is shown in FIGS. 1 and 4), extends through the neck portion 39 and into communication with the rod receiving groove 38. Once a spinal rod 2 or 3 has been positioned within the rod receiving groove 38, the set screw 20 may be threadedly advanced into the threaded bore 42 to engage the spinal rod 2 or 3 to secure the spinal rod 2 or 3 within the groove 38 and prevent rotation or sliding of the rotating connector 32 relative thereto.

Figure 25:
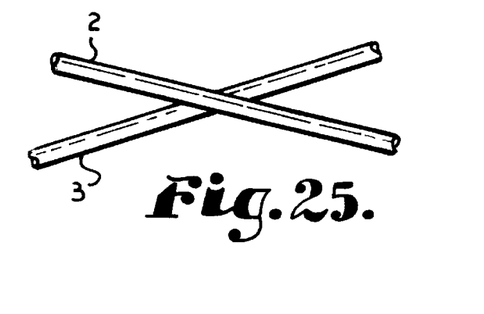
FIG. 25 is a side view of a pair of rods showing an exaggerated skewed configuration wherein the rods are spaced, non-parallel and non-coplanar.

The first transverse connection system 1 is particularly well adapted for maintaining spinal rods 2 and 3 in a generally parallel, but skewed alignment as shown in FIG. 4, wherein the angle of orientation of the axis of one spinal rod 2 relative to the spine 5 is different from the angle of orientation of the axis of the other spinal rod 3. Rods 2 and 3 are shown in a skewed configuration in FIG. 25. The degree to which spinal rod 3 is skewed relative to spinal rod 2 is exaggerated in FIGS. 4 and 25 for purposes of illustration. The sliding relationship between the base connector 10 and rotating connector 32 facilitates adjustments to the length of the first transverse connection system 1 to accommodate differences in spacing between the spinal rods 2 and 3. The ability of the rotating connector 32 to rotate relative to the base connector 10 facilitates adjustments to the rotational orientation of the rotating connector 32 relative to the base connector 10 to accommodate differences in the degree to which one spinal rod 2 is skewed relative to the other spinal rod 3.

Figure 5:
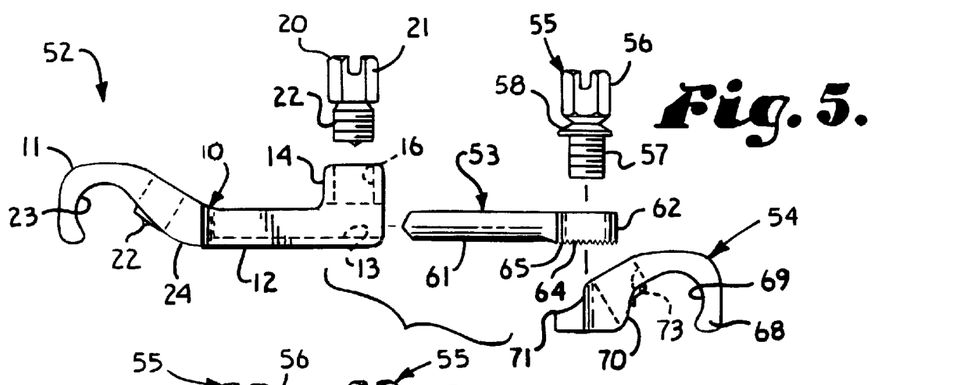
FIG. 5 is an exploded and enlarged side elevational view of the second transverse connection system, shown in FIG. 2.
Figure 6:
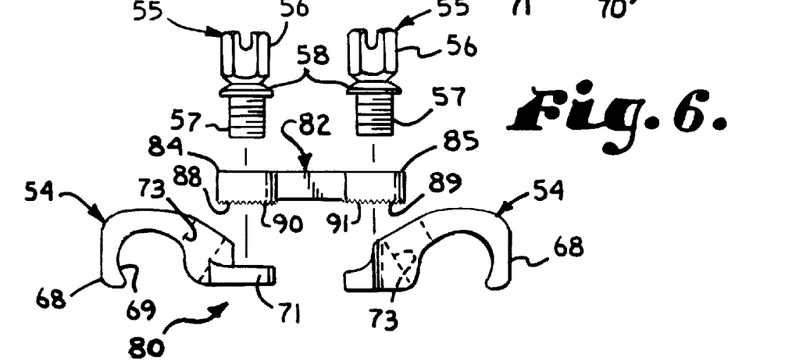
FIG. 6 is an exploded and enlarged side elevational view of the third transverse connection system, shown in FIG. 3.
Figure 7:
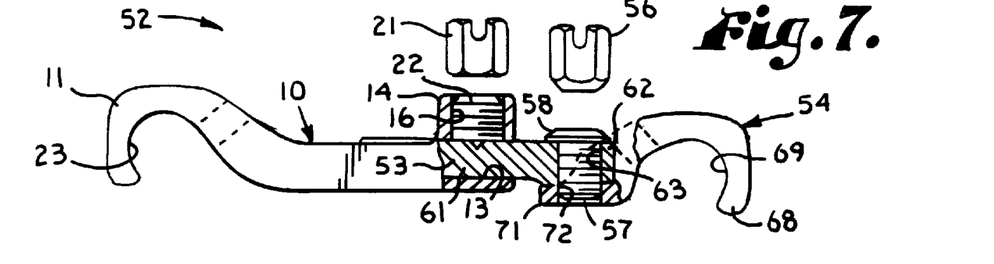
FIG. 7 is an enlarged side elevational view of the second transverse connection system with portions broken away to show use of a set screw and a flanged screw with the system.

A second transverse connection system 52 is shown in FIGS. 2, 5 and 7. The second transverse connection system 52 includes a base connector 10 as discussed above, a rotating link 53, and a hooked pivot connector 54. A flanged screw 55 (see FIG. 19), having a break off head 56, threaded end 57 and flange 58 is used to secure the rotating link 53 to the hooked pivot connector 54, as discussed in more detail below.

Figure 8:
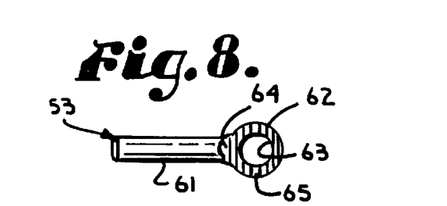
FIG. 8 is a an enlarged bottom plan view of a rotating link of the second transverse connection system.

The rotating link 53 includes a cylindrical shaft 61 and an eyelet 62 at one end of the shaft 61 with an opening 63 extending through the eyelet 62, as best seen in FIG. 8. A plurality of friction inducing ridges 64 with relatively sharp peaks are formed on a lower surface 65 of the eyelet 62 (see FIG. 8).

Figure 10:
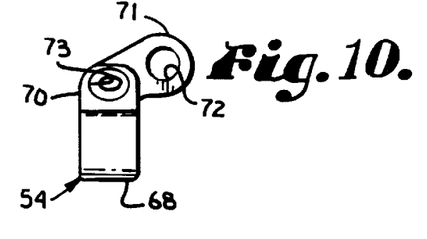
FIG. 10 is a top plan view of a right handed hooked pivot connector.

The hooked pivot connector 54 includes a hook or hooked end 68, a rod receiving groove 69 formed in the hook 68 and sized to receive a spinal rod 2 or 3, a neck or stem portion 70 and an eyelet 71, as best seen in FIG. 10. A first threaded bore 72, sized to receive one of the flanged screws 55 extends through eyelet 71. The neck portion 70 forms a transition with the eyelet 71. The eyelet extends away from the hook 68 at an angle relative thereto. A second threaded bore 73, sized to receive a set screw 20, extends through the neck portion 70 and into communication with the rod receiving groove 69. Once a spinal rod 2 or 3 has been positioned within the rod receiving groove 69, the set screw 20 may be threadedly advanced into the second threaded bore 73 to engage the spinal rod 2 or 3, to secure the spinal rod 2 or 3 within the groove 69 and prevent rotation of the hooked pivot connector 54 relative thereto.

The hooked pivot connector 54 is securable to the rotating link 53 by placing the eyelet 62 of the rotating link 53 in overlapping relationship with the eyelet 71 of the hooked pivot connector 54 such that the opening 63 is aligned with the first threaded bore 72 and then advancing the threaded end 57 of the flanged screw 55 through the opening 63 of the eyelet 62 and into threaded engagement with the first threaded bore 72 in the eyelet 71 until tight. The flanged screw 55 is then further tightened to draw the eyelets 62 and 71 toward the flange 58 of the flanged screw 55 such that the eyelet 71 of the hooked pivot connector 54 is drawn tightly against the ridges 64 of the eyelet 62 of the rotating link 53 and the eyelet 62 is drawn tightly against the flange 58. The orientation of the hooked pivot connector 54 relative to the rotating link 53 may be varied, to accommodate variations in the degree of divergence of the spinal rods 2 and 3, by pivoting the hooked pivot connector 54 relative to the rotating link 53, while maintaining the eyelets 62 and 71 aligned, and then fixing the orientation by securing the hooked pivot connector 54 to the rotating link 53 with flanged screw 55.

The cylindrical shaft 61 of the rotating link 53 is sized to fit within the cylindrical bore 13 of the first connector 10 to permit rotation of the rotating link 53 and the hooked pivot connector 54 connected thereto relative to the base connector 10 and to permit the hook 68 of the hooked pivot connector 54 to be slidingly advanced toward and away from the first hooked end 11 of the base connector 10. The pivot at the set screw 55 allows for adjustment of divergence while rotation of rotating link 53 allows for adjustment of skew within the same unit.

In particular, the rotating link 53 and the hooked pivot connector 54 connected thereto are rotatable relative to the base connector 10 to accommodate situations where the orientation of the spinal rods 2 and 3 is skewed. The sliding relationship between the base connector 10 and the hooked pivot connector 54 is used to accommodate differences in the distances between spinal rods 2 and 3.

Figure 9:
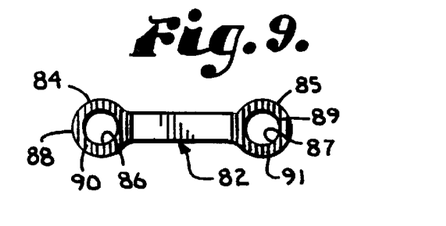
FIG. 9 is an enlarged and bottom plan view of a cross link of the third transverse connection system

FIG. 3 shows a third transverse connection system 80 comprising a pair of hooked pivot connectors 54 secured to spinal rods 2 and 3 and a cross link 82. The cross link 82 is secured to the hooked pivot connectors 54 by flanged screws 55. The cross link 82 includes first and second eyelets 84 and 85 at opposite ends thereof. As best seen in FIG. 9, openings 86 and 87 extend through eyelets 84 and 85 respectively and a plurality of friction inducing ridges 88 and 89 are formed on lower surfaces 90 and 91 respectively of the eyelets 84 and 85 respectively.

Hooked pivot connectors 54 are secured to the cross link 82 by aligning the eyelets 71 of the hooked pivot connectors 54 with a respective eyelet 84 or 85 on the cross link 82 and then threadingly advancing a flanged screw 55 through the aligned opening 86 and the threaded bore 72 of one hooked pivot connector 54 and aligned opening 87 and threaded bore 72 of the other hooked pivot connector 54. The orientation of the hooked pivot connectors 54 relative to the cross link 82 is adjusted to accommodate variations in the degree of divergence of the spinal rods 2 and 3 before the set screws 55 are tightened.

The hooked pivot connectors 54 shown in FIGS. 2, 3, 5, 6 and 7 may generally be referred to as right handed hooked pivot connectors 54, in that the eyelet 71 of each connector 54 is generally angled to the right when the connector 54 is viewed from the hooked end 68, as in FIG. 10. The structure forming the eyelet 71 is generally angled at an angle of approximately sixty degrees relative to an axis drawn through the hooked end 68.

Figure 11:
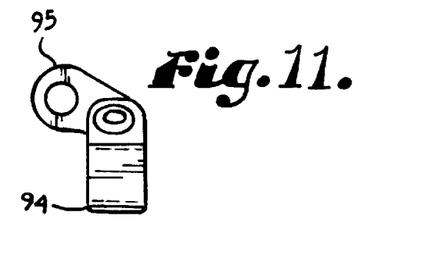
FIG. 11 is a top plan view of a left handed hooked pivot connector.
Figure 12:
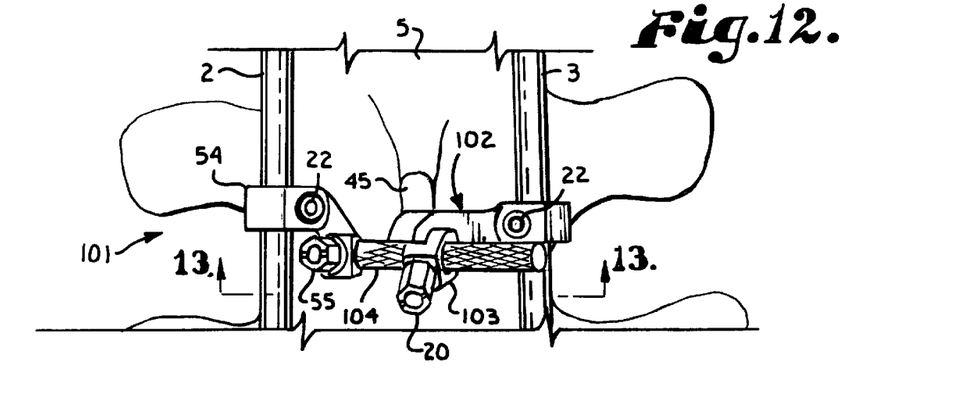
FIG. 12 is a fragmentary view of a spinal column with a corrective implant system incorporating a fourth transverse connection system of the present invention shown extending over and across a spinous process.

FIG. 11 is a top plan view of a left handed hooked pivot connector 94 wherein an eyelet 95 of the left handed pivot connector 94 is generally angled to the left when the connector 94 is viewed from the hooked end. Left handed hooked pivot connectors 94 may be substituted for any of the right hand hooked pivot connectors 54 shown in the different connection systems depending upon the conditions encountered.

Figure 13:
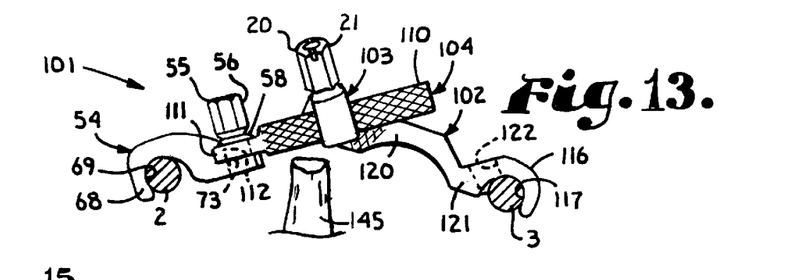
FIG. 13 is an enlarged and fragmentary view taken along line 13—13 of FIG. 12.

FIGS. 12 through 15 show a fourth transverse connection system 101. The fourth transverse connection system includes a lateral connector 102, a locking pivot mount 103, a knurled rotating link 104 and a hooked pivot connector 54 of the type described above. The knurled rotating link 104 is similar in construction to the rotating link 53 and includes a cylindrical shaft 110 and an eyelet 111 at one end thereof with an opening 112 extending through the eyelet 111. The knurled rotating link 104 is securable to a hooked pivot connector 54 using the flanged screw 55 threadingly inserted through the opening 112 in eyelet 111 and through threaded bore 72 in eyelet 71 of the hooked pivot connector 54, as shown in FIG. 13. Although the eyelet 111 is shown without ridges formed on a lower surface thereof it is foreseen that such ridges could be formed on the lower surface of the eyelet 111 to provide greater friction with respect to the hooked pivot connector 54. The outer surface of the shaft 110 of rotating link 104 is knurled and is generally longer than the shaft 61 of rotating link 53.

The lateral connector 102 includes a hooked end 116 with a spinal rod receiving groove 117 formed therein. The rod receiving groove 117 is sized to receive one of the spinal rods 2 or 3. The lateral connector 102 also includes a pivot mount support arm 120 connected to the hooked end 116 by a neck or stem portion 121 which forms a transition between the hooked end 116 and the pivot mount support arm 120. A threaded bore 122, sized to receive a set screw 20, extends through the neck portion 121 and into communication with the rod receiving groove 117 of the hooked end 116. Once a spinal rod 2 or 3 has been positioned within the rod receiving groove 117, the set screw 20 may be threadingly advanced into the threaded bore 122 to engage the spinal rod 2 or 3 to secure the spinal rod 2 or 3 within the groove 117 and prevent rotation or sliding of the lateral connector 102 relative thereto.

Figure 14:
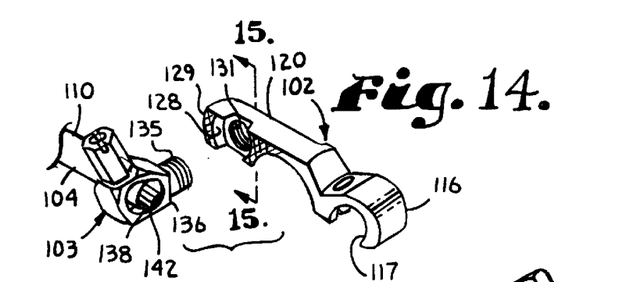
FIG. 14 is an enlarged and exploded view of a portion of the fourth transverse connection system.
Figure 15:
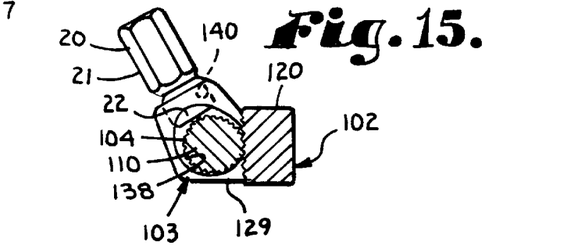
FIG. 15 is an enlarged cross-sectional view of the fourth transverse connection system, taken along line 15—15 of FIG. 14.

As best seen in FIG. 14, a cylindrical recess 128 extends into the pivot mount support arm 120 from an inner surface 129 thereof and at an end of the support arm 120 opposite the hooked end 116. The inner surface 129 of the support arm 120 is knurled. A threaded bore 131 extends through the support arm 120 centrally relative to the cylindrical recess 128.

The locking pivot mount 103 includes a threaded stud 135 extending from a nose 136 thereof. An ovate slot or opening 138 extends through the locking pivot mount 103 from the nose 136 toward an opposite end thereof. A threaded bore 140 extends through the pivot mount 103 from an upper and rearward end thereof and into communication with the ovate slot 138. The threaded bore 140 is generally angled toward the nose 136 of the pivot mount 103. The threaded bore 140 is sized to receive a set screw 20 with a break off head.

The threaded stud 135 is threadingly securable within threaded bore 131 extending through the pivot mount support arm 120 such that the nose 136 of the pivot mount 103 extends into the cylindrical recess 128. The nose 136 and recess 128 are sized to permit free rotation of the nose 136 within the recess 128, when loose. The nose 136 of the pivot mount 103 is threadingly advanced into the recess until a leading edge 142 of the ovate slot 138 extends into the recess 128.

With the tip of the set screw 20 secured within the threaded bore 140 of the pivot mount 103, an end of the shaft 110 of the rotating link 104 is extended through the ovate slot 138 in the pivot mount 103. The pivot mount 103 freely pivots to permit the shaft 110 to be positioned at an infinite number of various angles relative to the pivot mount support arm 120 to accommodate situations where a straight connection between spinal rods 2 and 3 is not possible, as generally shown in FIGS. 9 and 10 wherein the connection system 101 extends across and over a spinous process 145 of a vertebra. The shaft 110 is also rotatable and slidable within the slot 138 of the pivot mount 103. After the desired position and orientation of the shaft 110 relative to the pivot mount support arm 120 is obtained, the position of the shaft 110 relative t o the support arm 120 may be fixed by threadingly advancing the set screw 20 into ovate slot 138 such that the tip of the set screw 20 engages the shaft 110 of the rotating link 104 and advances the shaft 110 toward the leading edge 142 of the slot 138 and into engagement with the inner surface 129 of the support arm 120. The knurled finish of the shaft 110 and the inner surface 129 of the pivot mount support arm 120 enhance the frictional engagement between the shaft 110 and the inner surface 129 of the pivot mount support arm 120 thereby fixing the position and orientation of the shaft 110 relative to the support arm 120. The set screw 20 is tightened until a preselected torque is reached and the head 21 shears off. The connector 102 allows adjustment for arc, divergence and skew simultaneously.

Throughout the connector system the set screw 20 is generally used to secure various components to a selected rod or shaft to fix the relative orientation of the component to the rod or shaft. The set screw 20 is shown in greater detail in FIGS. 16 through 18. As noted above, the set screw 20 includes a break-off head 21 and a lower threaded portion 22. The head 21 has a hexagonal external cross-section and a round internal cross-section although it is foreseen that the internal cross-section could be hexagonal or other shapes to correspond to a hexagonal shaped tool or the like. The head 21 is relatively elongated to facilitate manipulation of the set screw 20.

Figures 16, 17, 18:
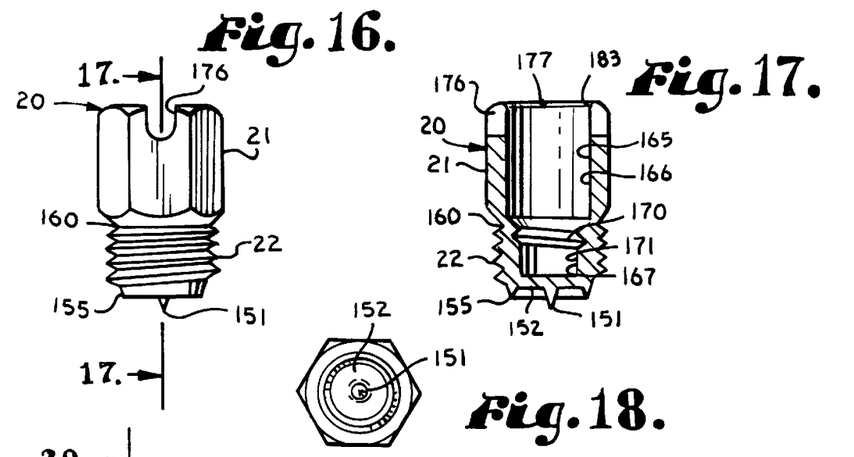
FIG. 16 is a front elevational view of a set screw with a break off head utilized with the transverse connection systems of the present invention.
FIG. 17 is a cross-sectional view, of the set screw, taken along line 17—17 of FIG. 16.
FIG. 18 is a bottom plan view of the set screw shown in FIG. 16.

A point or tip 151 is formed on a lower surface 152 of the set screw 20 centrally thereof so as to extend outward along a central axis of rotation of the set screw 20. The tip 151 is adapted to dig into a structure against which the screw 20 is driven such as cylindrical shaft 33 of rotating connector 32 forming a groove or indentation therein. A circumferential ring or ridge 155 is also formed on the lower surface 152 of the set screw 20. The ring 155 encircles and is radially spaced outward from the tip 151. A lower edge of the ring is sharp and is also adapted to dig into a structure against which the screw 20 is driven forming a groove or indentation therein. The tip 151 preferably extends axially outward and downward further than the ring 155 to penetrate deeper into the structure during use.

A peripheral break inducing notch 160 is formed between the head 21 and the lower threaded portion 22 of the set screw 20 on an outer surface 161 of the set screw 20. The notch 160 is positioned and sized (i.e. depth) to initiate breakage along the radially innermost portion thereof at a preselected torque without forming substantial burrs on the resulting upper surface of the set screw lower portion 22.

As best seen in FIG. 17 a cylindrical bore or projection receiving bore 165, comprising an upper bore section 166 and a lower bore section 167 is formed in the set screw 20 and extends through the head 21 and partially through the set screw lower threaded portion 22. The upper bore section 166 generally extends coaxially with the head 21 of the screw 20 and the lower bore section 167 extends partially through the lower threaded portion 22 of the screw 20. The lower bore section 167 is of a slightly smaller diameter than the upper bore section 166. A reverse thread 170, preferably of at least one half turn, is formed along an internal wall 171 of the set screw 20 which defines the lower bore section 167, near an upper end thereof, as shown in FIG. 17.

A drive slot 176 is formed in the set screw head 21 at an upper end 177 thereof. The slot 176 is a notch extending downward from the upper end 177 with portions on opposite sides of the screw 20. The set screw 20 is preferably driven by a hexagonal socket type wrench 179, partially shown in FIG. 21; however, the drive slot 176 is adapted to also receive a screw driver or set screw holder type tool for driving the set screw 20 into a selected threaded bore.

In use, the set screw 20 may be inserted in the set screw receiving bore such as threaded bore 16 of the base connector 10, as generally shown in FIGS. 5 and 7 after the base connector 10 and rotating link 53 are positioned in the desired orientation within the bore 13 of connector 10. To secure the cylindrical shaft 61 in position, thereby preventing further rotational or translational movement of the shaft 61 relative to the bore 13 of connector 10, the set screw 20 is further driven into the threaded bore 16 until the pointed tip 151 engages and bites into the shaft 61. Further driving or tightening of the set screw 20 produces torque on the head 21 and once sufficient torque is applied the head 21 of the set screw 20 shears off, as generally shown in FIG. 7. Penetration of the pointed tip 151 into the shaft 61 ensures secure fixation the set screw 20 relative to the shaft 61, so that the set screw 20 is able to secure the shaft 61 and prevent relative movement of the shaft 61 with respect to the base connector 10 even under substantial load.

The lower threaded portion 22 of the set screw 20 is preferably sized such that after the head 21 is sheared off, an upper surface of the set screw lower portion 22 is generally flush with an upper edge or upper surface of the boss 14 of the base connector 10 such that no portion of the set screw lower portion 22 extends beyond the upper surface boss 14. Further, after the head 21 is sheared off, the upper surface of the set screw lower portion 22 is generally free from burrs or jagged edges.

The set screw 20 may also be pre-loaded into the base connector 10, or related structure, prior to insertion into the patient. For example, the set screw 20 may be manually inserted in the threaded bore 16 of the base connector 10, or related item before insertion in a patient and rotated a sufficient number of turns such that the set screw 20 is secured in the set screw receiving bore 16, but such that the pointed tip 151 does not extend substantially into the cylindrical shaft receiving bore 13 in the bearing arm 12 and the juncture is sufficiently loose to allow the surgeon to adjust the various elements to the correct position. The shaft 61 of the rotating link 53 is positioned within bore 13 and the set screw 20 is positioned within threaded bore 16 without tightly engaging shaft 61, such that shaft 61 is easily movable relative to bore 13. The assembly is then placed on the spinal rods 2 and 3 and with the rotating link 53 positioned in the desired orientation the set screw 20 is tightened, as discussed above to fix the orientation of the rotating link 53 to the base connector 10.

Figures 21, 22:
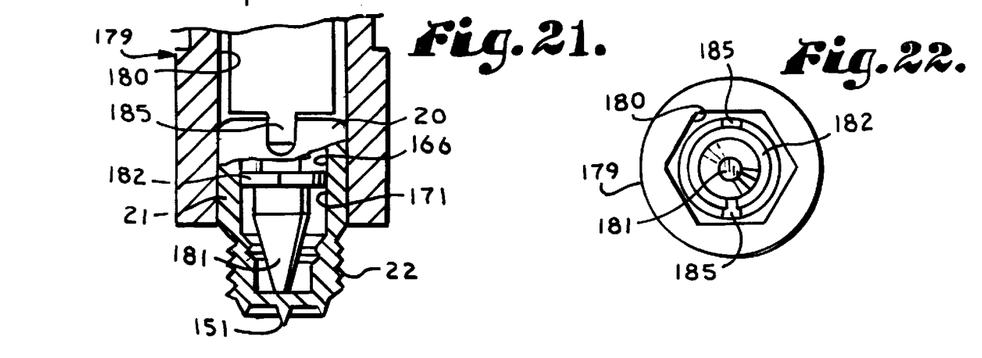
FIG. 21 is a fragmentary cross sectional view of the set screw of FIG. 16 shown secured within a socket wrench.
FIG. 22 is a bottom plan view of the socket wrench, as shown in FIG. 21, without a set screw secured therein.

The upper bore section 166 of the set screw 20 is adapted to facilitate removal of the set screw head 21 once it is sheared off from the lower threaded portion 22. The set screw 20 is adapted for use with the socket type torque wrench 179, as shown in FIG. 21, having a hexagonal socket 180 and a male member or projection 181 extending centrally in the socket 180. The projection 181 includes a resilient biasing member 182 circumferentially secured thereon. The projection 181 is sized for insertion into at least the upper bore section 166 when the set screw head 21 is positioned in the socket 180. The resilient biasing member 182 biases against the internal wall 171 of the head 21 defining the upper bore section 166 to grip the head 21.

The internal wall 171 has a chamfer 183 at the top end 172 of the set screw head 21 to facilitate insertion of the projection 181 into the projection receiving bore 165 in part by facilitating compression of the resilient biasing member 182. The resilient biasing member 182, as shown in FIGS. 21 and 22, generally comprises a split washer type spring, however it is foreseen that the biasing element 182 may be of a wide range of configurations and structures. Further other retention devices for releasably securing the set screw 1 to the projection 182 may be utilized including a rubber washer, magnetic coupling means, and various structure producing an interference fit between the projection 181 and the projection receiving bore 165.

The projection 181 may include a pair of drive projections or tabs 185 extending laterally from opposite sides of the projection 181 and adapted to mate with the drive slot 176 extending across the top end 177 of the set screw head 21 to permit an installing surgeon to drive or rotate the set screw 20 by the projection 181.

Figure 23:
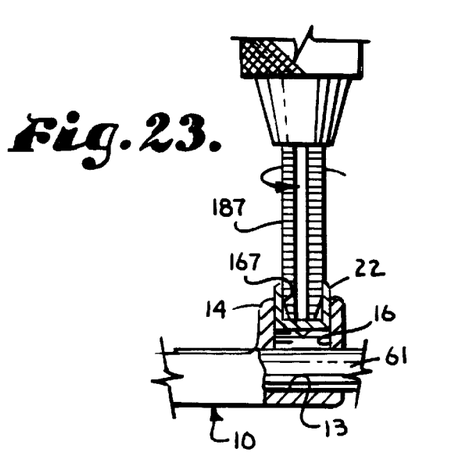
FIG. 23 is a side elevational view of the connection system of FIG. 7 showing use of an easy out type tool to remove a lower threaded portion of the set screw.
Figure 24:
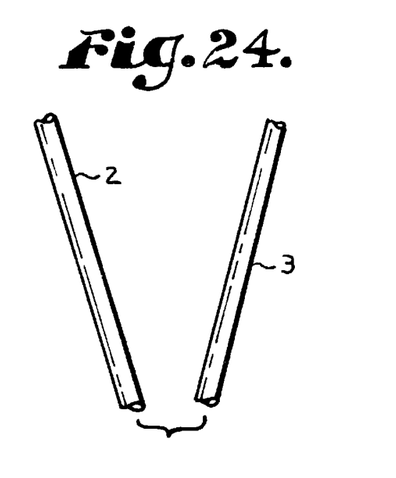
FIG. 24 is a top plan view of a pair of rods showing an exaggerated divergent configuration wherein the rods are coplanar but not parallel.

After the head 20 has been sheared off from the set screw lower threaded portion 22, the lower bore section 167 is adapted to receive an easy out type tool 187 to permit removal of the set screw lower portion 22 when necessary. The reverse thread 170 facilitates starting the easy out type tool 187 by allowing the tool 187 to get an initial grasp after which it would be expected to cut further into the lower bore 167.

Although specifics relating to the use of set screw 20 were described with reference to fixing the relative orientation of cylindrical shaft 61 of rotating link 53 relative to the cylindrical bore 13 of base connector 10, the method of use, installation and retrieval of set screw 20 is similar for fixing the relative orientation of the shaft 33 of rotating link 32 in cylindrical bore 13 of base connector 10, first and second hooked ends 11 and 34 of the first transverse connection system 1 to spinal rods 2 and 3, hooked end 68 of hooked pivot connectors 54 to spinal rods 2 and 3, hooked end 116 of lateral connector 102 to spinal rod 2 or 3 and lateral connector 102 to shaft 110 of knurled rotating link 104.

Figure 19:
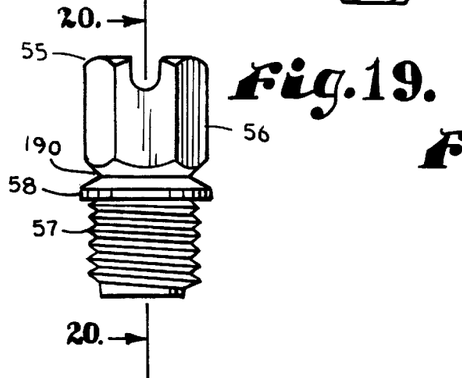
FIG. 19 is a front elevational view of a flanged screw with a break off head utilized with the transverse connection systems of the present invention.
Figure 20:
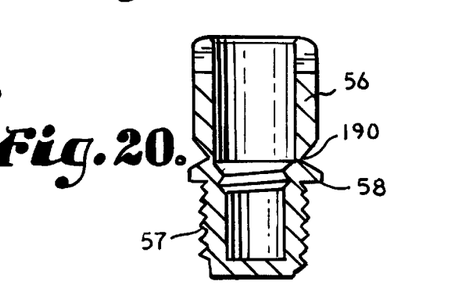
FIG. 20 is a cross-sectional view of the flanged screw, taken along line 20—20 of FIG. 19.

The flanged screw 55, FIGS. 19 and 20, is particularly well adapted for securing together two components having overlapping eyelets. Flanged screw 55 is of similar construction to set screw 20 except that the lower threaded portion 57 of screw 55 is longer than the threaded portion 22 of screw 20, the bottom of the lower threaded portion 57 of screw 55 is flat and screw 55 includes the flange or circumferential shoulder 58 extending just below a peripheral notch 190. The rest of the flanged screw 55 is generally the same as set screw 20, including the internal construction thereof.

The flanged screw 55 is particularly well adapted for securing together two components after the desired pivotal, rotational and angular relationship between the two has been selected. For example, as noted above the flanged screw 55 is used for securing hooked pivot connector 54 to rotating link 53 in the second transverse connection system 52, as shown in FIGS. 5 and 7. The hooked pivot connector 54 is preferably loosely secured to the rotating link 53 using the flanged screw 55 prior to insertion in a patient. Once the assembly is inserted and the desired pivotal relationship between the hooked pivot connector 54 is established relative to the rotating link 53, the flanged screw 55 is tightened, utilizing a tool such as wrench 179, until sufficient torque is applied and the head 56 shears off along the peripheral notch 190 and preferably without burrs and with only the flange 58 extending above the rotating link 53.

The flanged screw 55 is used in a similar manner in securing cross link 82 to hooked pivot connectors 54 and to secure knurled rotating link 104 to the hooked pivot connector 54.

The components of the transverse connection systems described above are designed to have relatively low profiles to facilitate insertion of the implant and reduce discomfort associated with use of the implant. For example, the neck portions of the various hooked connectors such as neck portions 24, 39, 70 and 121 of the base connector 10, hooked rotating connector 32, hooked pivot connector 54 and lateral connector 102 respectively, slope downward from the hooked end to reduce the profile thereof. A semi-circular cutout 192 is formed in the lateral connector 102 of the fourth transverse connection system 101 to reduce the profile thereof.

It is to be understood that while certain forms of the present invention have been illustrated and described herein, it is not to be limited to the specific forms or arrangement of parts described and shown.

What is claimed and desired to be secured by Letters Patent is as follows:

1. A transverse connection system for making a rigid connection between two spinal rods comprising:
    a) a first connector having a first hooked end adapted to be secured to one of said spinal rods and having a shaft receiving bore formed in a second end thereof and having a threaded bore extending into said shaft receiving bore proximate said second end of said first connector;
    b) a second connector having a second hooked end adapted to be secured to a second of said spinal rods and having a shaft positionable within said shaft receiving bore in said first connector for rotational and sliding advancement relative thereto prior to securement thereof, such that said shaft is variably positionable in said bore during installation to allow for variance in spacing and skew of the rods;
    c) a set screw threadingly received within said threaded bore to secure and fix the orientation of said second connector shaft within said first connector shaft receiving bore; and
    d) at least one of said first hook and said second hook being joined to said shaft receiving bore and said shaft respectfully by a connection that is pivotal during installation so as to allow adjustment of the system for use wherein the spinal rods diverge.

2. A hooked pivot connector adapted to permit connection of a transverse connection system to a pair of spinal rods extending along the spine of a patient at varying degrees of divergence; said hooked pivot connector comprising:
    a) a hooked end having a spinal rod receiving groove formed therein; said spinal rod receiving groove sized to receive a spinal rod therein;
    b) a threaded bore extending through a neck of said hooked pivot connector and opening into said rod receiving groove;
    c) a set screw threadingly advanceable within said threaded bore of said neck for engaging and fixing the relative position of a spinal rod positioned within said rod receiving groove; and
    d) an eyelet extending rearward from said neck of said pivot connector.

3. The hooked pivot connector as in claim 2 wherein:
    a) said eyelet extends rearward from said neck thereof at an angle of between approximately 30 to 90 degrees relative to an axis extending through said second hooked end and perpendicular to a front edge thereof.

4. A transverse connection system set comprising a plurality of interchangeable components for making rigid connections between two spinal rods and to accommodate variations in the alignment, and orientation of the spinal rods, said components comprising:
    a) at first base connector having a first hooked end adapted to be secured to one of said spinal rods and having a shaft receiving bore formed in a second end thereof and having a threaded bore extending into said shaft receiving bore proximate said second end of said first connector;
    b) a hooked rotating connector having a second hooked end adapted to be secured to one of said spinal rods and having a first shaft extending rearwardly therefrom; said first shaft selectively positionable within said shaft receiving bore in said first base connector for rotational and sliding advancement relative thereto prior to selective securement thereof;
    c) a hooked pivot connector having a third hooked end adapted to be secured to one of said spinal rods and further including a first eyelet extending rearward from said third hooked end;
    d) a rotating link having a second shaft and a second eyelet formed on one end of said shaft; said second shaft is selectively positionable within said shaft receiving bore in said first base connector for rotational and sliding advancement relative thereto prior to selective securement thereof;
    e) a set screw threadingly received within said threaded bore of said first base connector to selectively secure and fix the orientation of said first shaft or said second shaft within said first base connector shaft receiving bore.

5. The connection system set as in claim 4 further including:
    a) a flanged screw sized for insertion through said first and second eyelets and for threading engagement of at least a lowermost of said first and second eyelets when positioned in overlapping relationship for fixing the pivotal orientation of said hooked pivot connector relative to said rotating link.

6. The connection system set as in claim 4 wherein said set further comprises:
    a) a plurality of said hooked pivot connectors; and b) a cross link having third and fourth eyelets formed at opposite ends thereof.

7. The connection system set as in claim 6 further including:
   a) a plurality of flanged screws adapted for interchangeably securing said rotating link to one of said hooked pivot connectors through insertion of one of said flanged screw through said first and second eyelets positioned in overlapping relationship or for securing said cross link to a pair of said hooked pivot connectors through insertion flanged screws through said third and fourth eyelets of said cross link and aligned first eyelets of said hooked pivot connectors positioned in positioned in overlapping relationship.

8. The transverse connection system set as in claim 4 further comprising:
   a) a second base connector having fourth hooked end adapted to be secured to one of said spinal rods and having a support arm extending rearwardly of said fourth hooked end;
   b) a pivot mount having a shaft receiving first bore formed therein for selectively receiving said shaft of said rotating link; said pivot mount pivotally mounted to said support arm; a threaded second bore extending through said pivot mount and opening into said shaft receiving first bore; and
   c) a set screw threadingly securable within said threaded second bore in said pivot mount for engaging said shaft of said rotating link to fix the orientation of said rotating link shaft within said shaft receiving first bore.

9. A transverse connection system for making a rigid connection between two spinal rods comprising:
   a) a first connector having a first hooked end adapted to be secured to one of said spinal rods and having a shaft receiving bore formed in a second end thereof and having a threaded bore extending into said shaft receiving bore proximate said second end of said first connector;
   b) a second connector having a second hooked end adapted to be secured to a second of said spinal rods and having a shaft positionable within said shaft receiving bore in said first connector for rotational and sliding advancement relative thereto prior to securement thereof;
   c) a set screw threadingly received within said threaded bore to secure and fix the orientation of said second connector shaft within said first connector shaft receiving bore;
   d) said second hooked end being part of a hooked pivot connector further including a first eyelet extending rearward from said second hooked end; and
   e) said shaft being part of a rotating link having a second eyelet formed on one end of said shaft.

10. The connection system as in claim 9 including:
   a) a flanged screw sized for insertion through said first and second eyelets and for threading engagement of at least a lowermost of said first and second eyelets when positioned in overlapping relationship for fixing the pivotal orientation of the hooked pivot connector relative to the rotating link.

11. The connection system as in claim 9 wherein:
   a) said first eyelet extends rearwardly of said second hooked end at an angle of between approximately 30 to 90 degrees relative to an axis extending through said second hooked end and perpendicular to a front edge thereof.

12. The connection system as in claim 9 wherein:
   a) a plurality of pointed friction inducing ridges are formed on a surface of said rotating link eyelet which is adapted to be positioned in abutting relationship with a surface of said hooked pivot connector eyelet.

13. A transverse connection system for making a rigid connection between two spinal rods comprising:
   a) a first connector having first hooked end adapted to be secured to one of said spinal rods and having a support arm extending rearwardly of said first hooked end;
   b) a pivot mount having a shaft receiving first bore formed therein; said pivot mount pivotally mounted to said support arm; a threaded second bore extending through said pivot mount and opening into said first bore;
   c) a second connector having a second hooked end adapted to be secured to a second of said spinal rods and having a shaft extending rearwardly therefrom; said shaft securable within said shaft receiving first bore in said pivot mount for rotational and sliding advancement relative thereto;
   d) a set screw threadingly securable within said threaded second bore in said pivot mount for engaging said shaft to fix the orientation of said second connector shaft within said shaft receiving first bore;
   e) said shaft receiving first bore being oblong and said pivot mount being pivotally securable to said support arm such that a portion of said pivot mount extends into a recess extending in a first side of said support arm such that a leading edge of said shaft receiving bore extends into said recess; and
   f) said threaded bore being positioned such that said threaded bore opens into said shaft receiving first bore on a side generally opposite a leading edge thereof, such that advancement of said set screw against said shaft within said shaft receiving bore advances said shaft into engagement with said first side of said support arm creating frictional engagement therebetween and preventing the pivot mount from thereafter pivoting relative to the support arm and preventing rotational or sliding advancement of the shaft relative to the shaft receiving first bore.

14. The connection system as in claim 13 wherein:
   a) said second hooked end is part of a hooked pivot connector further including a first eyelet extending rearward from said second hooked end; and
   b) said shaft is part of a rotating link having a second eyelet formed on one end of said shaft.

15. The connection system as in claim 14 including:
   a) a flanged screw sized for insertion through said first and second eyelets and for threading engagement of at least a lowermost of said first and second eyelets when positioned in overlapping relationship for fixing the pivotal orientation of the hooked pivot connector relative to the rotating link.

16. The connection system as in claim 14 wherein:
   a) said first eyelet extends rearwardly of said second hooked end at an angle of between approximately 30 to 90 degrees relative to an axis extending through said second hooked end and perpendicular to a front edge thereof.

* * * * *